United States Patent [19]

Berndt

[11] Patent Number: 5,693,122
[45] Date of Patent: Dec. 2, 1997

[54] BASIC STRUCTURE FOR A LIQUID CHROMATOGRAPHY DEGASSER

[75] Inventor: Manfred Berndt, Waldbronn, Germany

[73] Assignee: Hewlett Packard Company, Palo Alto, Calif.

[21] Appl. No.: 574,874

[22] Filed: Dec. 18, 1995

[30] Foreign Application Priority Data

Dec. 23, 1994 [DE] Germany ............ 44 46 270.0

[51] Int. Cl.⁶ ............................................. B01D 19/00
[52] U.S. Cl. ................................... 96/6; 96/7; 96/14
[58] Field of Search ............................. 95/46; 96/4, 6, 96/7, 11–13

[56] References Cited

U.S. PATENT DOCUMENTS

| | | | |
|---|---|---|---|
| 2,618,357 | 11/1952 | Harlow | 96/7 |
| 3,354,618 | 11/1967 | Dounoucos | 96/7 |
| 3,369,343 | 2/1968 | Robb | 95/46 |
| 3,416,985 | 12/1968 | Dounoucos | 96/7 X |
| 3,520,803 | 7/1970 | Iaconelli | 96/13 X |
| 3,564,819 | 2/1971 | Neulander et al. | 96/7 |
| 3,735,562 | 5/1973 | Mousseau, Jr. et al. | 96/6 |
| 3,822,601 | 7/1974 | Borom | 96/12 X |
| 3,998,593 | 12/1976 | Yoshida et al. | 96/6 X |
| 4,190,426 | 2/1980 | Ruschke | 96/6 |
| 4,422,936 | 12/1983 | Riede et al. | 96/6 X |
| 4,469,495 | 9/1984 | Hiraizumi et al. | 96/6 |
| 4,729,773 | 3/1988 | Shirato et al. | 96/6 |
| 4,853,013 | 8/1989 | Rio et al. | 96/6 |
| 4,999,107 | 3/1991 | Guerif | 96/7 X |
| 5,019,140 | 5/1991 | Bowser et al. | 96/6 |
| 5,053,060 | 10/1991 | Kopf-Sill et al. | 95/46 |
| 5,091,080 | 2/1992 | van Eikeren et al. | 95/46 X |
| 5,126,045 | 6/1992 | Kohlheb et al. | 96/4 X |
| 5,183,486 | 2/1993 | Gatlen et al. | 96/6 X |
| 5,225,080 | 7/1993 | Karbachsch et al. | 96/4 X |
| 5,290,340 | 3/1994 | Gatten et al. | 95/46 |
| 5,536,405 | 7/1996 | Myrna et al. | 96/7 X |

FOREIGN PATENT DOCUMENTS

| | | | |
|---|---|---|---|
| 0106523 | 4/1984 | European Pat. Off. | 96/7 |
| 0377067 | 7/1990 | European Pat. Off. | 96/4 |
| 3122186A1 | 12/1982 | Germany . | |
| 61-171522 | 8/1986 | Japan | 96/7 |
| 62-042708 | 2/1987 | Japan | 96/6 |
| 1-176421 | 7/1989 | Japan | 96/7 |
| 6-007630 | 1/1994 | Japan | 96/4 |

*Primary Examiner*—Robert Spitzer

[57] ABSTRACT

A basic structure for a liquid chromatography degasser, includes a supporting structure with a perimeter encompassing an opening in which support ribs are arranged. The opening is covered by a membrane made from a material with a good permeability index. Two basic structures are combined to form a basic module. A liquid chromatography degasser comprises at least one or a plurality of basic modules, which are stacked on top of each other, whereby a micro-vacuum-pump is arranged at the top of the stack, and an inlet and an outlet for the liquid being degassed are provided at the bottom of the stack.

22 Claims, 9 Drawing Sheets

BASIC STRUCTURE FOR A LIQUID CHROMATOGRAPHY DEGASSER

DESCRIPTION

The invention described herein refers to a liquid chromatography degasser. This invention is especially concerned with a basic structure and a basic module for a vacuum online degasser.

In liquid chromatography the task of the degasser is to reduce the amount of gases dissolved in the solvents employed. The solvents used in liquid chromatography are usually stored in contact with the surrounding air, i.e., they are usually in a gas-saturated state. These dissolved gases adversely affect chromatography.

If a solvent mixture is used (e.g. alcohol/water) the gas solubility of the mixture may be less than that of the liquids it contains. This leads to the formation of gas bubbles, which have detrimental effects on the stability of the system flow and the composition of the solvents. This effect plays an especially important role in so-called low-pressure mixture systems.

Oxygen dissolved in a solvent adversely affects detection sensitivity. The high solubility of oxygen in eluents is noted with UV detection, and large fluctuations of the oxygen concentration can lead to marked detection noise at wavelengths below 260 nm. The high absorbance can even be used to measure oxygen content.

In fluorescence the so-called quenching effect occurs, which can lead to fluorescence detection being suppressed. For this reason, sensitive measurements with a fluorescence detector can only be conducted using degassed solvents.

Apart from the influence of dissolved gases on detection, chemical reactions of dissolved gases with the eluents also present a problem. This can adversely affect analysis results, especially in biological experiments.

Because of the aforementioned adverse effects of dissolved gases on analysis results, it is absolutely imperative to degas the liquid being analyzed.

Several methods are known in the prior art, including for example baking, boiling, ultrasonic degassing, helium degassing and vacuum degassing.

These methods are sufficiently well-known.

It has recently been the so-called online vacuum degassing which has proved to be advantageous, and its use is spreading.

An example of a vacuum online degasser is described for instance in the product description "The HP 1050 Series Online Degasser".

Figure 8:
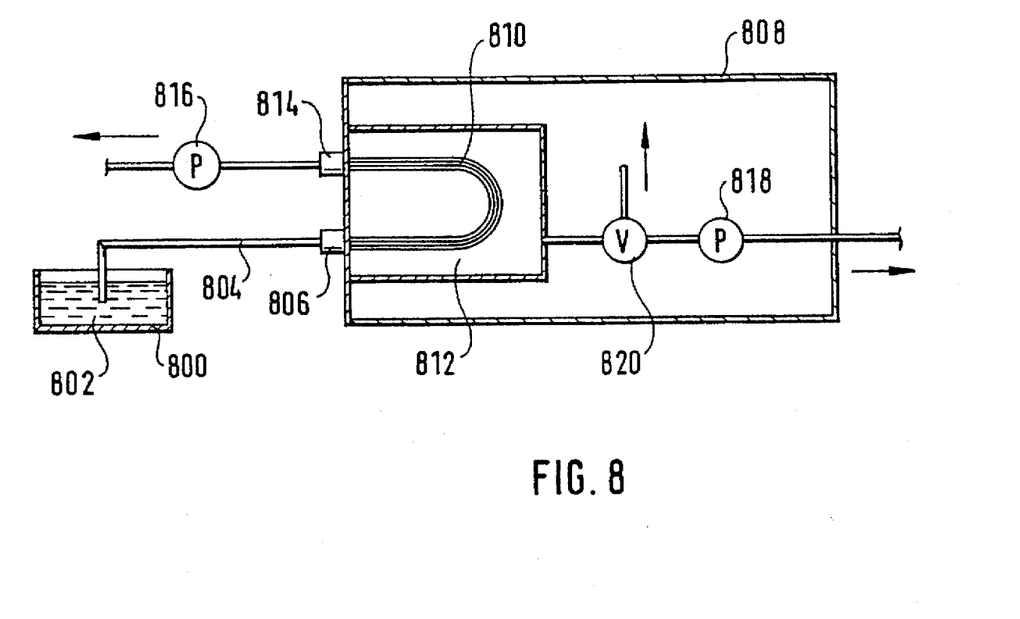
FIG. 8 shows a prior art vacuum online degasser.

The principle on which this vacuum online degasser is based will now be described in more detail with reference to FIG. 8.

The solvent being degassed, which is in the solvent vessel 800, is fed into the inlet connection of the degasser 808 via feed line 804. The inlet connection 806 is connected to a plurality of parallel flexible tubes 810 which are arranged inside a vacuum chamber 812 of degasser 808. The ends of tubes 810 opposite the inlet connection 806 are connected to outlet connection 814 of the degasser 808. By means of a pump 816 the degassed solvent is delivered to the chromatograph for analysis.

In the vacuum chamber 812, a partial vacuum is produced using a vacuum pump 818. Between the vacuum chamber 812 and the vacuum pump 818 there is a valve 820.

The tubes 810 arranged in the vacuum chamber 812 are made of a thin-walled PTFE material (PTFE= polytetrafluoroethylene), since this material has good permeability and resistance to chemicals.

Vacuum pump 818, which is a so-called 2-stage vacuum pump, produces an average partial vacuum of about 600 mbar.

During the flow of the solvent through the flexible tubes 810, the gases dissolved in the solvent diffuse through the walls of the tubes. Depending on the implementation, the gas content of the solvent is reduced to below 1 ppm oxygen.

U.S. Pat. No. 4,469,495 describes a degasser for removing oxygen or other dissolved gases from a liquid used in liquid chromatography, in which the liquid being degassed is passed through a spiral-shaped tube. This tube is made of a synthetic resin material, such as tetrafluoroethylene.

U.S. Pat. No. 4,729,773 describes a device for degassing liquids in which the liquid is passed through a tube made of a fluorine resin, which allows gases to pass through it while preventing the liquid from doing so.

The technologies described above depend mainly on the use of a thin-walled flexible or rigid tube, which may be made from PTFE, for instance. Several such tubes are used in parallel to increase the active diffusion surface area.

One drawback of this technology lies in the fact that the manufacture of a flexible or rigid tube with as thin a wall as possible has technological limitations. Thin-walled flexible or rigid tubes are complicated to manufacture and to handle, and their use incurs an increase in costs.

A further drawback lies in the fact that the dimensions of the flexible or rigid tube can vary depending on the liquid being degassed. This means that for different liquids, with different gases and gas concentrations, different tube configurations must be provided. Because of the technological limitations described above, this involves considerable complexity and high costs.

Compared to the prior art, the objective of the invention is to produce a basic structure for a liquid chromatography degasser by means of which a thin membrane becomes easy and economical to manufacture and the device simple to use.

This objective is satisfied by a basic structure according to claim 1.

A further objective of the present invention is to produce a basic module for a liquid chromatography degasser which can be manufactured easily and economically and which is simple to use.

This objective is satisfied by a basic module according to claim 12.

Yet another objective of the invention is to produce a liquid chromatography degasser which is easy to assemble, can be applied to the degassing of different liquids, is simple to use, and incurs low costs.

This objective is satisfied by a liquid chromatography degasser in accordance with claim 13 or claim 18.

The present invention provides a liquid chromatography degasser with the following characteristics:
 a supporting structure with a perimeter encompassing an opening, with support ribs arranged in the opening; and
 a membrane covering the opening.

The present invention provides a basic module for a liquid chromatography degasser with
 first and second basic structures, where the second basic structure is arranged on the first basic structure such that the surface of the second basic structure facing away from the membrane is adjacent to the surface of the first basic structure on which its membrane is situated, where the connection openings of the first basic structure are aligned with the respective passage openings or the second basic structure and the passage openings of the first basic structure are aligned with the respective connection openings of the second basic structure.

The present invention provides a liquid chromatography degasser with a basic module;

a first cover plate situated adjacent to that surface of the first basic structure of the basic module which is facing away from the membrane; and a second cover plate which is arranged adjacent to that surface of the second basic structure of the basic module on which the membrane of the second basic structure is situated;

where the first cover plate has two connection openings which are aligned with the passage openings of the first basic structure of the basic module;

where the second cover plate has two additional connection openings which are aligned with the passage openings of the second basic structure of the basic module; and where the surface of the second cover plate facing the membrane of the second basic structure of the basic module has a recess with support ribs.

The present invention provides a liquid chromatography degasser with a plurality of basic modules stacked on top of each other;

a first cover plate adjacent to that surface of the first basic structure of the bottommost basic module which is facing away from the membrane; and a second cover plate adjacent to that surface of the second basic structure of the topmost basic module on which the structure's membrane is situated;

where the first cover plate has two connection openings which are aligned with the passage openings of the first basic structure of the bottommost basic module;

where the second cover plate has two additional connection openings, which are aligned with the passage openings of the second basic structure of the topmost basic module; and where the surface of the second cover plate facing the membrane of the second basic structure of the topmost basic module has a recess with support ribs.

Examples of preferred embodiments of the invention will be described in more detail with reference to the accompanying drawings.

Before preferred embodiments of the present invention are described, the principles on which the vacuum online degasser is based will be described in the following.

Degassing relies on the diffusion of gases through a membrane. Diffusion occurs when a gas is mixed with another gas such that its concentration (partial pressure or partial density) differs from point to point. It is only completed when a homogeneous mixture has been formed. The mass $\Delta m$ of a gas which passes through a surface by means of diffusion is proportional to the area $\rho$ of the surface and to time $\Delta t$:

$$\Delta m = -D(d\rho/dx) \cdot \Delta t \qquad \text{Fick's First Law}$$

where D is the coefficient of diffusion in $cm^2 \cdot s^{-1}$.

Another variable to be considered is permeation. Permeation is understood to mean the diffusion of a gas through a wall or membrane. In the following, certain simplifications are assumed for calculating the diffusion process.

Under the following assumptions
static view, and
constant gas concentration in the liquid
the following equation applies:

$$P = (n \cdot s)/(A \cdot \Delta \rho \cdot t)$$

where
P=permeation
n=amount of gas diffused
s=thickness of membrane wall
A=surface area of membrane
t=time Therefore permeation can be increased by increasing the active surface area of the membrane or by decreasing the thickness of the membrane.

When degassing liquids, the choice of material for the membrane is crucial. In the prior art, flexible PTFE tubes (PTFE=polytetrafluoroethylene) are used. PTFE is characterized by a good permeability index.

Permeability is also heavily dependent on the crystallinity of the material. In general, PTFE is used for degassers. However, if necessary, FEP (fluorinated ethylene propylene), whose permeability index is less than that of PTFE, can also be used. It must be said, however, that where the level of crystallinity is high, the permeability of PTFE is on the same order of magnitude as that of FEP.

Other materials can also be used, such as fluorinated polymers with a high resistance to chemicals. Such fluorinated polymers include for instance PCTFE (polychlorotrifluoroethylene), ETFE or PVDF (polyvinylidene fluoride).

Unlike the prior art, the invention does not use flexible or rigid tubes but instead employs microsystem technology (for instance, the LIGA technique—Lithographie/Galvanik/Abformung, structuring by lithography and galvanic action). Microsystem technology enables microstructures to be produced cheaply in different materials, e.g. silicon, glass, ceramics or plastics.

Figure 1:
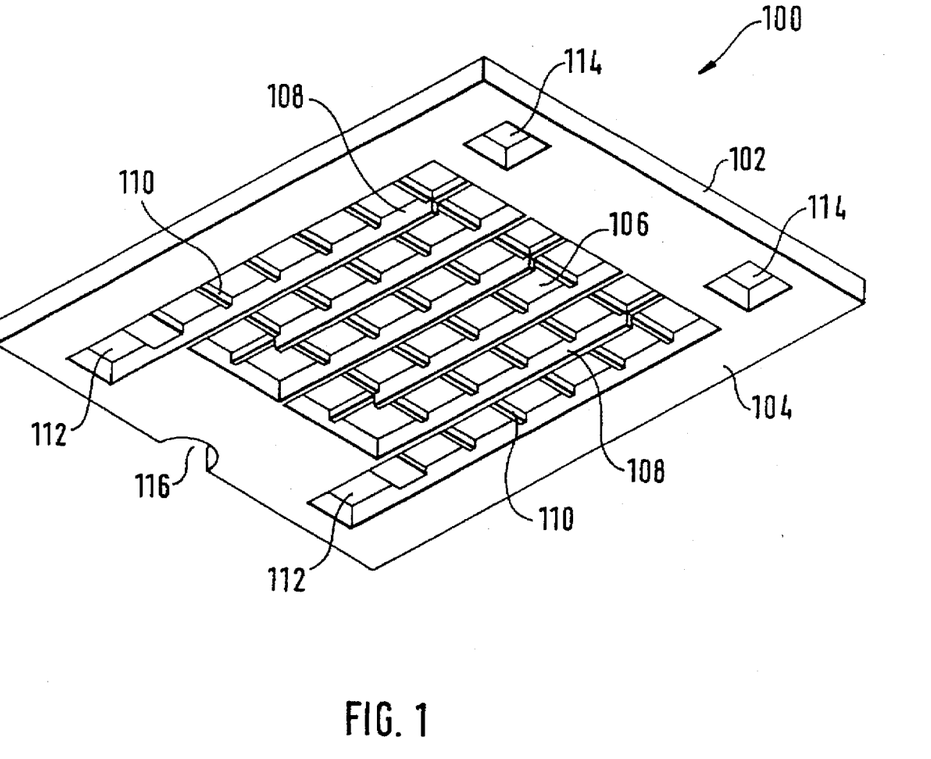
FIG. 1 shows an enlarged isometric view of the basic structure from below.

With reference to FIG. 1, a basic structure 100, representing the smallest unit, or basic element, for manufacturing a liquid chromatography degasser for vacuum online degassing, will now be described. The basic structure 100 comprises a supporting structure 102 which has a perimeter 104. This perimeter 104 encompasses an opening 106 in which a plurality of support ribs 108 are situated.

As FIG. 1 shows, the support ribs 108 are arranged in such a way that the opening 106 follows a meandering path, the support ribs 108 being of the same thickness as that of the supporting structure 102.

In addition, the basic structure 100 consists of transverse ribs 110 which are arranged at right angles to the support ribs 108 and are of a thickness less than that of the supporting structure 102.

Apart from opening 106, the perimeter 104 of supporting structure 102 has other openings. Two connection openings 112 are situated in the perimeter 104 and are connected to opening 106, and two passage openings 114 are provided in the perimeter 104. As FIG. 1 shows, the connection openings 112 and the passage openings 114 are arranged symmetrically to each other in this embodiment.

In order to distinguish between the side of the supporting structure 102 having the connection openings 112 and the side of the supporting structure having the passage openings 114, a mark 116 is present on the supporting structure 102 next to the connection openings 112.

Figure 2A:
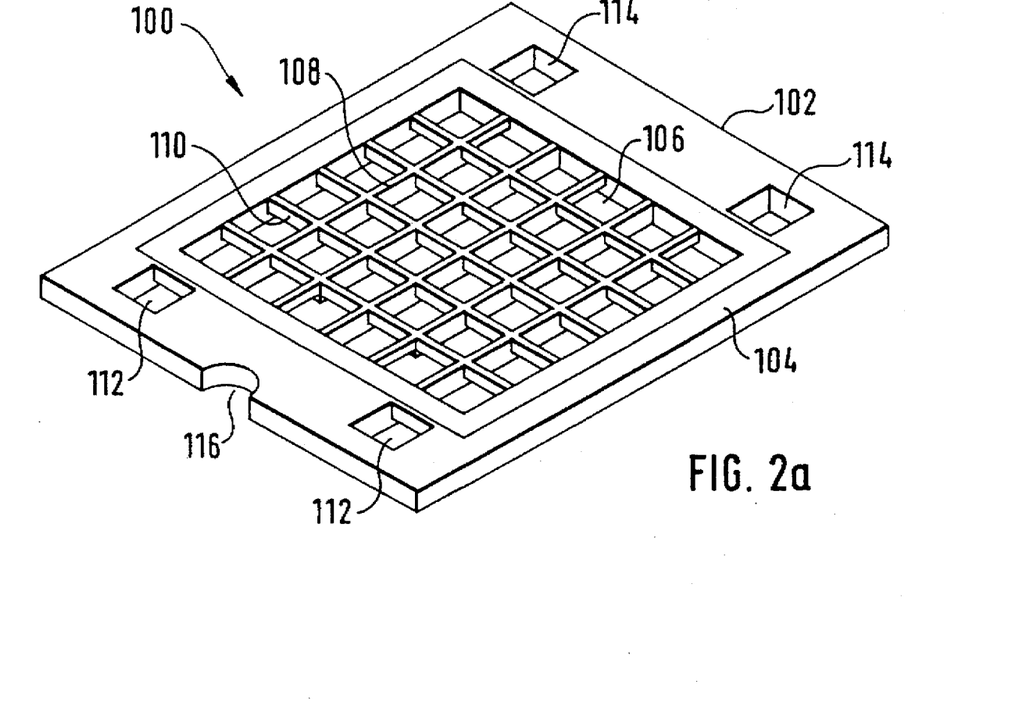
FIGS. 2a and 2b show the basic structure of FIG. 1 from above and below, respectively.
Figure 2B:
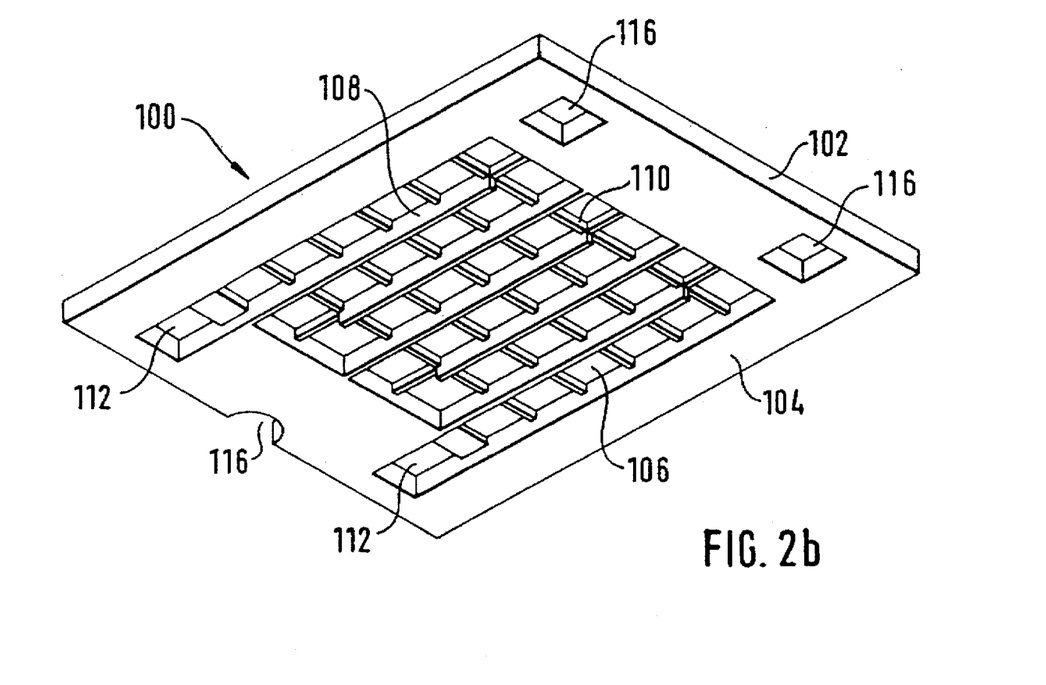

FIG. 2a and FIG. 2b show a further representation of the basic structure of FIG. 1 from above and below, respectively. The same reference symbols are used here as are used in FIG. 1.

Figure 3A:
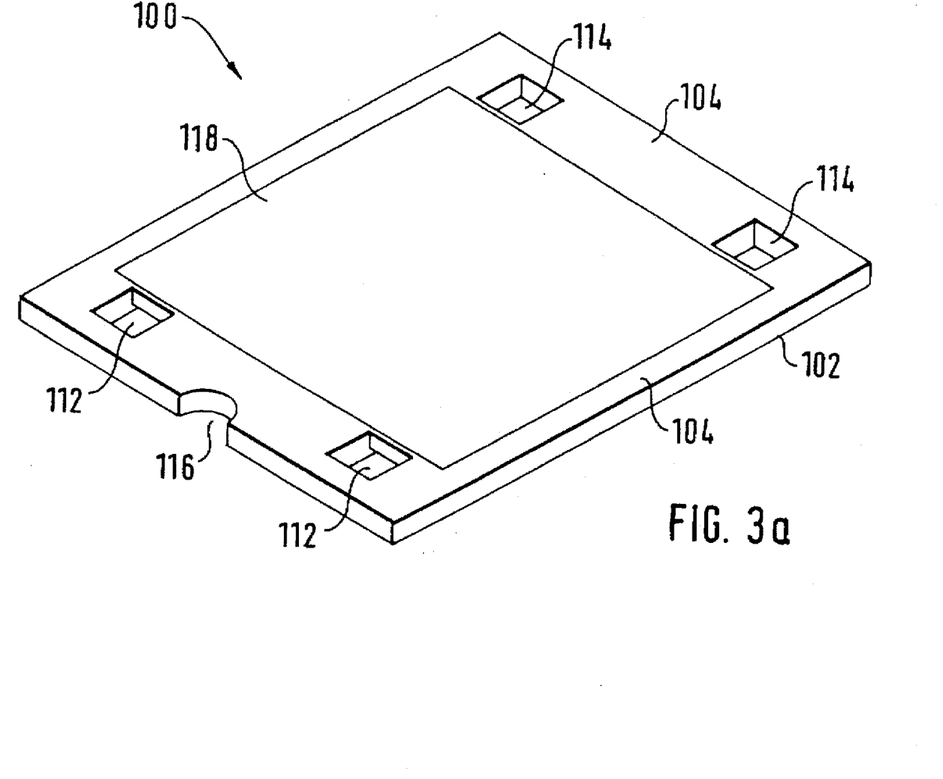
FIGS. 3a and 3b show the basic structure with a membrane, from above and below, respectively.
Figure 3B:
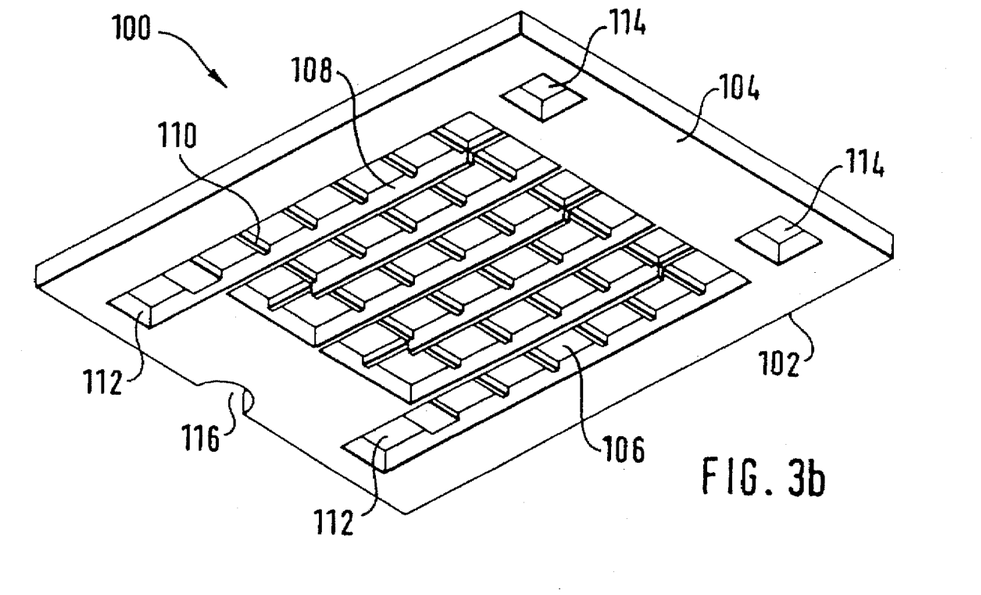

In FIGS. 3a and 3b the completed basic structure 100 is represented, in which a membrane 118 covers opening 106.

The basic structure shown in FIGS. 1 to 3 represents the basic element used in manufacturing a micro-degasser. The structure is implemented using microsystem technology, which is well-known among those skilled in the art.

The key element here is producing the very thin membrane 118. In a preferred embodiment the thickness of this membrane is only a few micrometers. In order to support the membrane, which is very unstable mechanically, support ribs 108 and transverse ribs 110 are provided. FIGS. 1 to 3 are merely schematic representations aimed at making the basic structure easier to understand. In practical embodiments of the invention, the size of the cells formed by the support ribs 108 and the transverse ribs 110 is in the micrometer range. These cells enable the membrane 118 to be thin and pressure-resistant.

Through the meandering arrangement of the support ribs 108, a meandering "channel" is formed on the underside of the basic structure 100. This enables a liquid being degassed to flow through the channel in a degasser comprising multiple basic structures. Depending on the number of basic structures used, the effective membrane area can be adjusted on the basis of the liquid to be degassed, its volume, the concentration of the gases dissolved therein, etc.

Membrane 118 is placed on the supporting structure 102 by means of conventional methods such as coating or deposition.

Membrane 118 consists of a material with a good permeability index, such as polytetrafluoroethylene (PTFE) or fluorinated ethylene propylene (FEP). In addition, other materials can be employed, such as all those belonging to the group of fluorinated polymers, which possess high resistance to chemicals. Such fluorinated polymers include for example PCTFE (polychlorotrifluoroethylene), ETFE or PVDF (polyvinylidene fluoride). Materials belonging to the polyolefins (e.g. polypropylene) can also be used. Polypropylene is uncritical with respect to the processes involved in microstructuring, and it is also very resistant to chemicals.

In the additional descriptions of the embodiment examples of the invention, the same reference symbols are used for the same elements in the following diagrams.

Figure 4A:
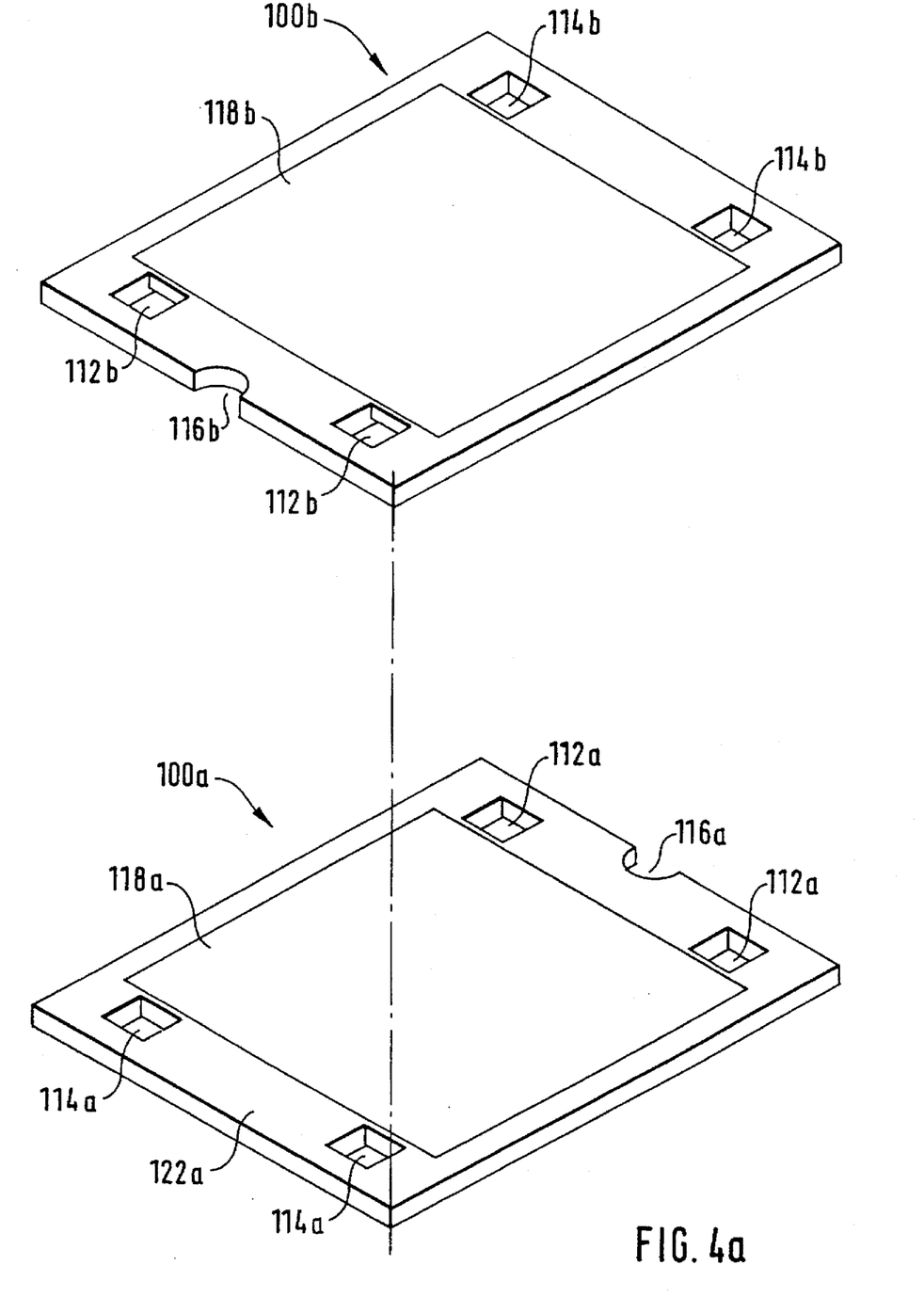
FIGS. 4a and 4b depict two basic structures forming a basic module, from above and below, respectively.
Figure 4B:
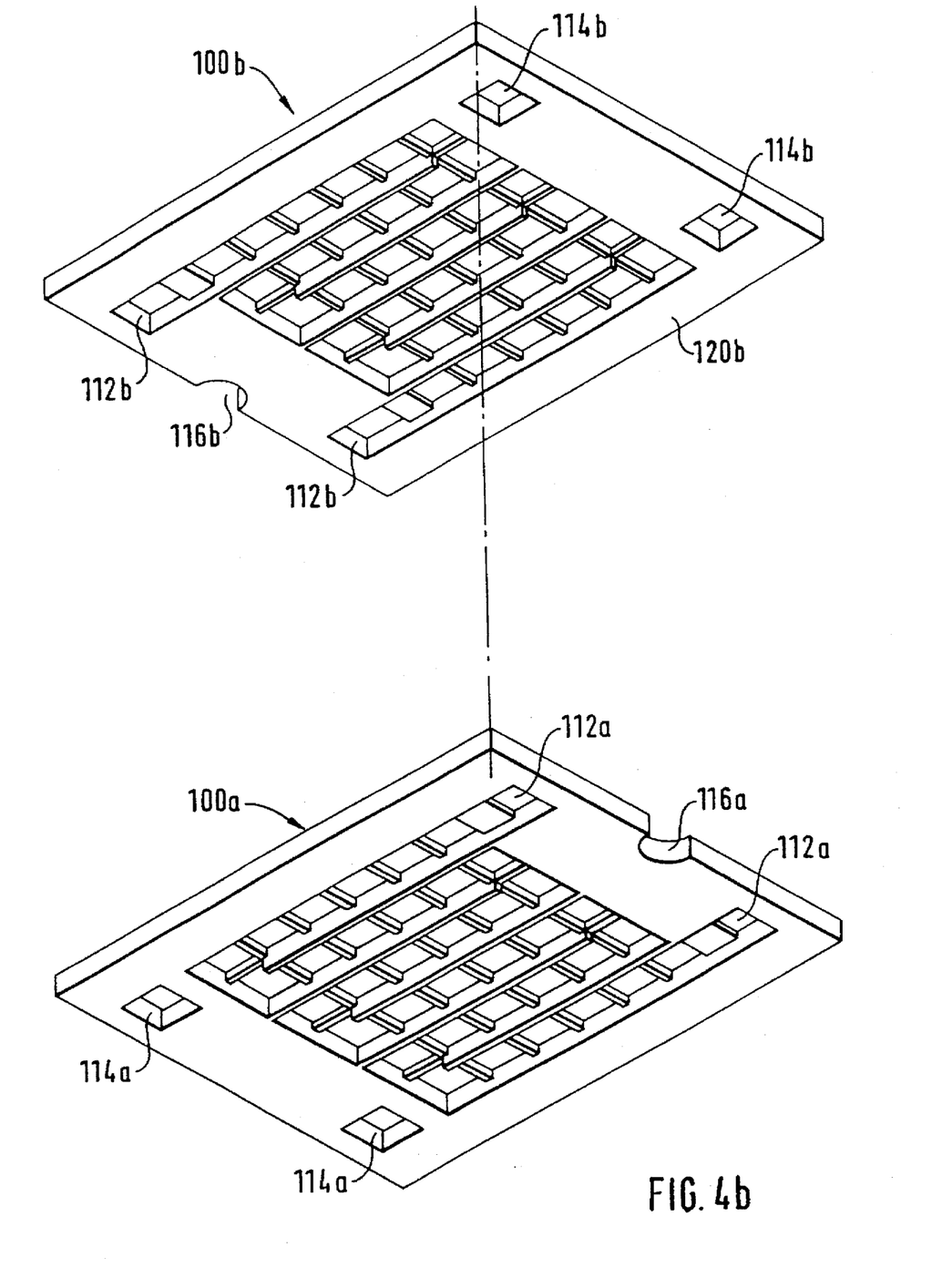

FIGS. 4a and 4b show how two basic structures 100a, 100b are joined to form a basic module.

As shown in FIGS. 4a and 4b, the basic structure 100b is arranged on basic structure 100a in such a manner that that surface 120b of basic structure 100b which faces away from membrane 118b is adjacent to that surface 122a of basic structure 100a on which its membrane 118a is situated.

The connection openings 112a of basic structure 100a are aligned with the respective passage openings 114b of basic structure 100b, and the passage openings 114a of basic structure 100a are aligned with the respective connection openings 112b of basic structure 100b.

As the diagrams in FIG. 4a and FIG. 4b show, the arrangement of basic structures 100a and 100b described above is simplified by the provision of marks 116a and 116b on the two basic structures, such that the two basic structures 100a and 100b are arranged with the marks 116a and 116b on opposite sides of the basic module thus formed.

Figure 5:
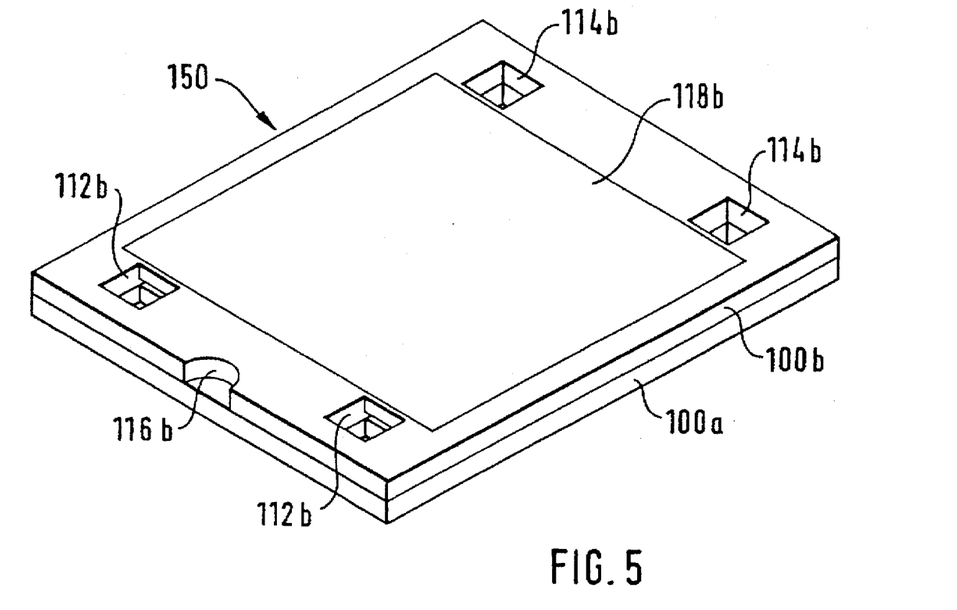
FIG. 5 shows a representation of the basic module.

FIG. 5 shows the basic module 150 which is formed thereby.

Basic structures 100a and 100b are joined to form basic module 150, using a joining technique common in microstructuring.

Figure 6:
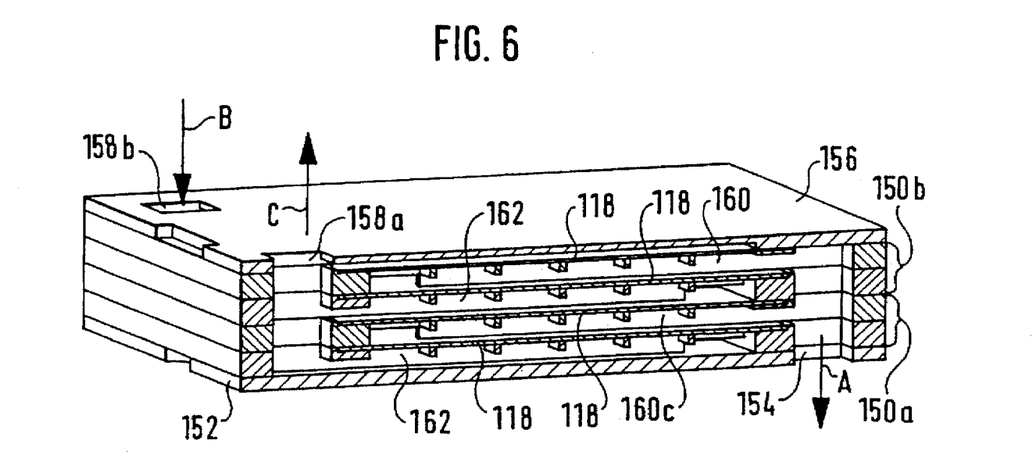
FIG. 6 shows a cross-section of a combination of two basic modules.

FIG. 6 shows combination of two basic modules 150a and 150b. The two basic modules 150a and 150b are stacked on top of each other. On the underside of basic module 150a, a first cover plate 152 is provided, which has an opening 154 aligned with the passage opening of the bottom basic structure of basic module 150a. On the upper basic module 150b a second cover plate 156 is arranged, which has an opening 158a and an opening 158b. These openings 158a and 158b are aligned with the passage openings of the upper basic structure of the upper basic module 150b.

By means of this combination of two basic modules 150a and 150b, two separate chambers 160 and 162 are formed, whereby the individual membranes, which are labeled with the general reference symbol 118, are arranged in parallel. This parallel arrangement is an important characteristic of the invention, since the efficiency of degassing can be optimized thereby while at the same time incurring low costs.

By attaching a vacuum pump (not shown) to the opening 154 of the first cover plate 152, and by connecting opening 158b to an inlet connection for letting in the liquid to be degassed and opening 158a to an outlet connection for letting out the degassed liquid, a micro-degasser is formed. With this micro-degasser, the vacuum is applied via an opening 154, as shown by arrow A; the solvent being degassed is let in via opening 158b, as shown by arrow B; it passes through the channels defined in the basic module and releases the gases dissolved in the solvent via the membrane; the degassed solvent leaves the micro-degasser via opening 158a, as shown by arrow C.

It is obvious to one skilled in the art that the number of basic modules 150a and 150b can be varied depending on the solvent being degassed, on the gases it contains and also on other parameters to be considered. For certain configurations, for instance, it may suffice to use a single basic module, whereas for other configurations several basic modules may be necessary.

Figure 7A:
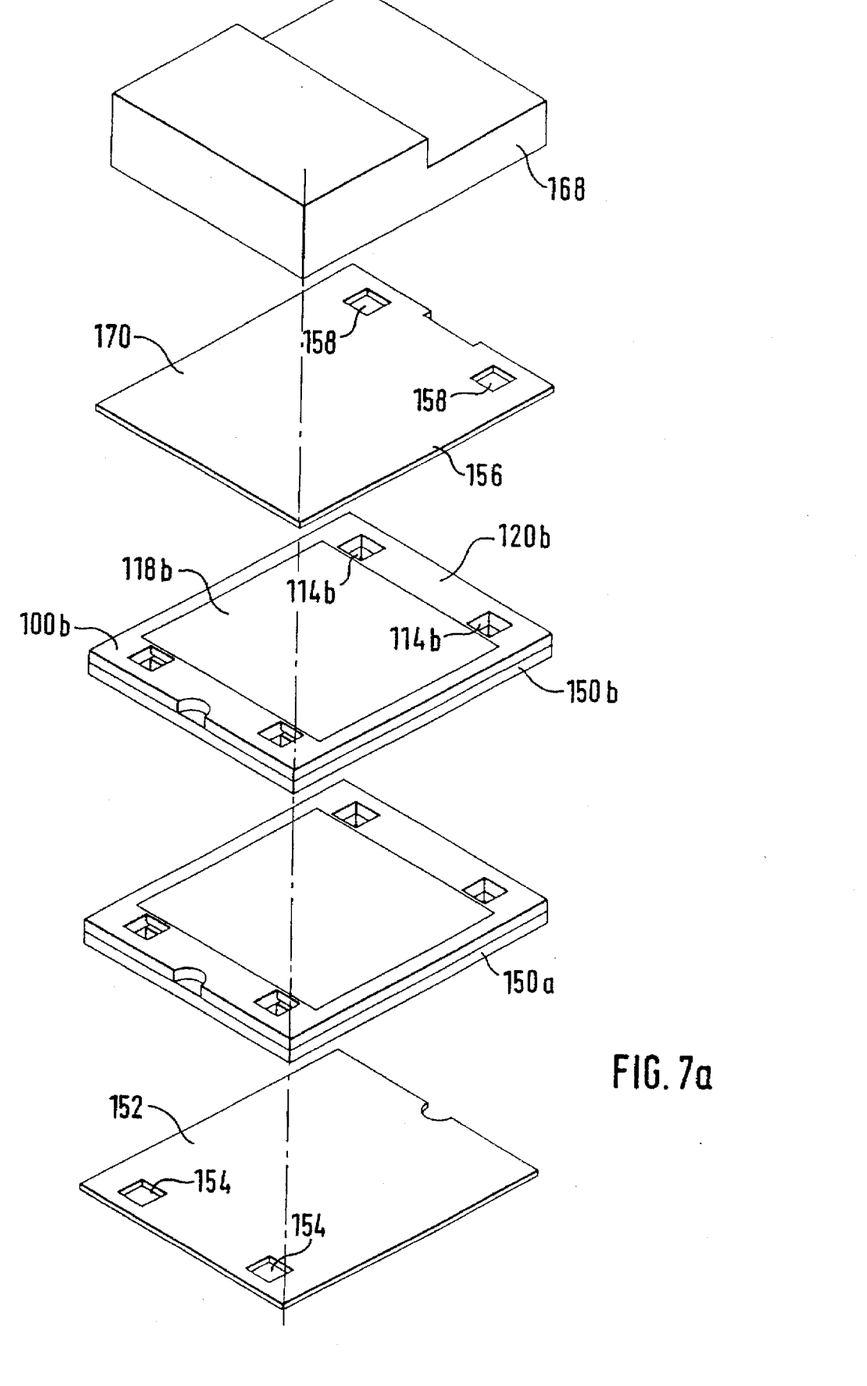
FIGS. 7a and 7b depict the assembly of a liquid chromatography degasser, from above and below, respectively.
Figure 7B:
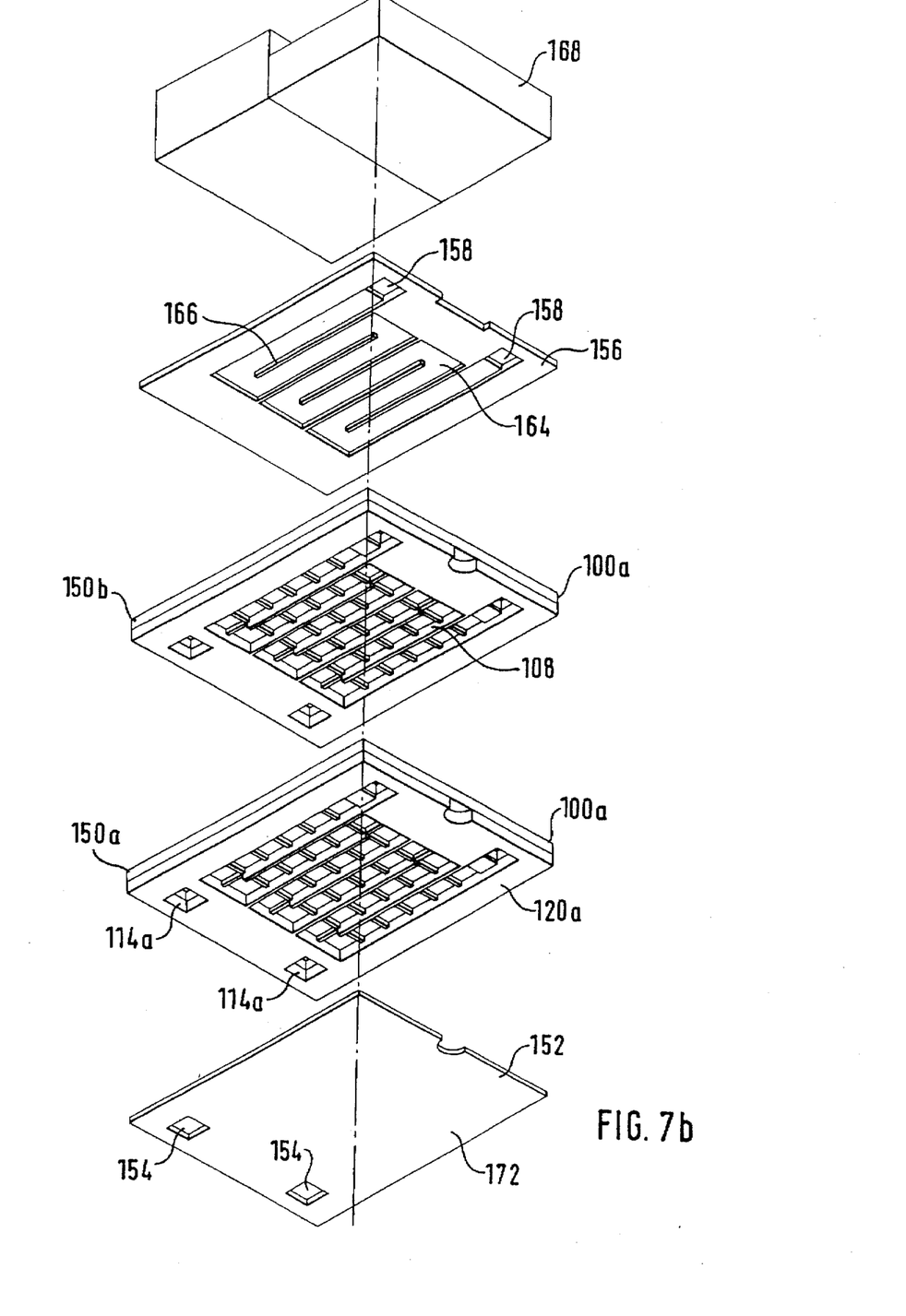

FIG. 7 shows the structure of a liquid chromatography micro-degasser with two basic modules.

The degasser shown in FIG. 7 consists of two basic modules 150a and 150b which are stacked on top of each other. Adjacent to that surface 120a of the first basic structure 100a of the bottommost basic module 150a which faces away from the membrane is the first cover plate 152, and adjacent to that surface 120b of the second basic structure 100b of the topmost basic module 150b on which the membrane of the structure is situated is the second cover plate 156.

The first cover plate 152 has two connection openings 154, which are aligned with the passage openings 114a of the first basic structure 100a of the bottommost basic module 150a. The second cover plate 156 has two additional connection openings 158, which are aligned with the passage openings 114b of the second basic structure 100b of the topmost basic module 150b. Also, the surface 122b of the second cover plate 156 which is facing membrane 118b of the second basic structure 100b of the topmost basic module 150b has a recess 164, this recess 164 having support ribs 166.

As can be seen in FIG. 7b, the support ribs 166 of the second cover plate 156 are aligned with the support ribs 108 of the first basic structure 100a of the topmost basic module 150b.

A vacuum pump 168 in microstructure technology is arranged on that surface 170 of the second cover plate 156 which faces away from the topmost basic module 150b.

It is obvious to those skilled in the art that the micro-vacuum-pump 168 can also be arranged on that surface 172 of the first cover plate 152 which is facing away from the bottommost basic module 150a.

It is also obvious that, in order to form a fluid link with the degasser, those openings which are not adjacent to the vacuum pump 168 are provided with an inlet and an outlet connection (in FIG. 7 these are connections 154 in the first cover plate 152), through which a liquid can be let in or let out.

Since the micro-degasser described above was manufactured with the help of microsystem technology, it is possible to combine the basic module with additional elements. For example, it is possible to integrate the relevant microvalves (such as for the inlet and outlet of the solvent being degassed) and the control electronics associated with them. It is also possible for instance to provide the degasser described in FIG. 7 with an oxygen sensor, in order to precisely control the degassing process in response to the output signals of this sensor (e.g., to control the micro-vacuum-pump).

The ability to combine the micro-degasser with other microsystem components represents an important characteristic of the present invention. In this way a completely integrated unit is formed, which as a whole has the following overall configuration:

one or more basic modules combined with
  a vacuum pump produced using microtechnology
  valves produced using microtechnology
  oxygen sensors/electronics produced using microtechnology.

I claim:

1. A basic structure for a liquid chromatography degasser, comprising:
   a supporting structure having opposed surfaces and a perimeter encompassing an opening, and with support means arranged in the opening between said opposed surfaces, said opening extending between said opposed surfaces;
   a membrane covering the opening at one of said opposed surfaces and positioned on said support means, said support means comprising elements arranged to support the membrane, said elements having at least a portion with a thickness of less than said supporting structure; and
   a further supporting structure and further membrane positioned at a second of said opposed surfaces and cooperating with said support means to provide a nonlinear flow path in said opening.

2. A basic structure according to claim 1, wherein the support means are support ribs arranged in the opening in such a way that the opening follows a meandering path, the support ribs being of a same thickness as a thickness of the supporting structure.

3. A basic structure according to claim 1, wherein said elements comprise:
   transverse ribs arranged at right angles to the support means.

4. A basic structure according to claim 1, further comprising:
   at least two connection openings connected to the opening and two passage openings situated in the perimeter.

5. A basic structure according to claim 4, wherein the connection openings and the passage openings are arranged symmetrically to each other.

6. A basic structure according to claim 4, in which the supporting structure has a mark adjacent to the connection openings.

7. A basic module for a liquid chromatography degasser, including first and second basic structures according to claim 4, wherein the second basic structure is arranged on the first basic structure in such a way that a surface of the second basic structure which faces away from the membrane is adjacent to a corresponding surface of the first basic structure on which said further membrane is situated, and where the connection openings of the first basic structure are aligned with the respective passage openings of the second basic structure, and the passage openings of the first basic structure are aligned with the respective connection openings of the second basic structure.

8. A liquid chromatography degasser, with a basic module according to claim 7, further comprising:
   a first cover plate arranged adjacent to that surface of the first basic structure of a basic module which faces away from the membrane; and
   a second cover plate arranged adjacent to that surface of the second basic structure of a basic module on which the further membrane of the second basic structure is situated;
   wherein the first cover plate has two connection openings which are aligned with the passage openings of the first basic structure of said basic module;
   wherein the second cover plate has two additional connection openings which are aligned with the passage openings of the second basic structure of said basic module; and
   wherein the surface of the second cover plate which faces the membrane of the second basic structure of said basic module has a recess with support ribs.

9. A degasser according to claim 8, wherein the support means of the second cover plate are aligned with the support means of the first basic structure of the basic module.

10. A degasser according to claim 8, further comprising:
   a micro-vacuum-pump arranged on that surface of the second cover plate which faces away from the basic module.

11. A degasser according to claim 8, further comprising:
   a micro-vacuum-pump arranged on that surface of the first cover plate which faces away from the basic module.

12. A degasser according to claim 8, which is an integrated unit which includes the basic module combined with a micro-vacuum-pump, valves, oxygen sensors and electronics, all produced using microtechnology.

13. A liquid chromatography degasser including a plurality of basic modules according to claim 7, which are stacked on top of each other;
   a first cover plate which is situated adjacent to that surface of the first basic structure of a bottommost basic module which faces away from the membrane;

a second cover plate which is arranged adjacent to that surface of the second basic structure of a topmost basic structure on which the further membrane of the second basic structure is situated;

wherein the first cover plate has two connection openings aligned with the passage openings of the first basic structure of the bottommost basic module;

wherein the second cover plate has two additional connection openings aligned with the passage openings of the second basic structure of the topmost basic module; and wherein that surface of the cover plate which faces the membrane of the second basic structure of the topmost basic module has a recess with support ribs.

14. A degasser according to claim 13, wherein the support ribs of the second cover plate are aligned with the support ribs of the first basic structure of the topmost basic module.

15. A degasser according to claim 13, in which a micro-vacuum-pump is arranged on that surface of the second cover plate which faces away from the topmost basic module.

16. A degasser according to claim 13, wherein a micro-vacuum-pump is arranged on that surface of the first cover plate which faces away from the bottommost basic module.

17. A degasser according to claim 13, which is an integrated unit comprising that plurality of basic modules which are combined with a micro-vacuum-pump, valves, oxygen sensors and electronics, all produced using microtechnology.

18. A basic structure according to claim 1, wherein the membranes consist of a material with a good permeability index.

19. A basic structure according to claim 18, wherein the membranes consist of polytetrafluoroethylene (PTFE).

20. A basic structure according to claim 18, wherein the membranes consist of fluorinated ethylene propylene (FEP).

21. (Amended) A basic structure according to claim 18, wherein the membranes are made from one of the materials belonging to the group of fluorinated polymers including PCTFE (polychlorotrifluoroethylene), ETFE or PVDF (polyvinylidene fluoride).

22. A basic structure to claim 18, wherein the membranes consist of one of the materials belonging to the polyolefin group, including polypropylene.

* * * * *